United States Patent [19]
Woodhouse et al.

[11] Patent Number: 5,105,806
[45] Date of Patent: Apr. 21, 1992

[54] RIGID ABDOMINAL PAD FOR LUMBAR/SACRAL SUPPORT

[75] Inventors: Michael L. Woodhouse; Lawrence M. Shall, both of Norfolk, Va.; Stephen M. Shall, Toledo, Ohio; Jack Booden, Jr., Norfolk, Va.

[73] Assignee: WBSS, Norfolk, Va.

[21] Appl. No.: 576,151

[22] Filed: Aug. 29, 1990

Related U.S. Application Data

[63] Continuation of Ser. No. 275,789, Nov. 23, 1988, abandoned.

[51] Int. Cl.⁵ .............................................. A61F 8/00
[52] U.S. Cl. ................................. 128/961; 128/112.1; 128/876; 128/78; 602/19
[58] Field of Search ................... 128/95.1, 96.1, 100.1, 128/106.1, 112.1, 876, 78

[56] References Cited

U.S. PATENT DOCUMENTS

| 1,052,523 | 2/1913 | Sillin | 128/96.1 |
|---|---|---|---|
| 1,401,056 | 1/1921 | Doyle . | |
| 1,571,420 | 2/1926 | Le Cras | 128/112.1 X |
| 1,918,022 | 7/1933 | Drey | 128/112.1 X |
| 1,992,397 | 2/1935 | Rowley | 128/96.1 |
| 2,222,488 | 11/1940 | Rich | 128/96.1 |
| 2,285,612 | 6/1942 | Rehthaler | 128/96.1 |
| 2,354,494 | 7/1944 | Ajdukovich | 128/112.1 X |
| 2,449,641 | 9/1948 | Cidissen | 128/96.1 |
| 2,828,737 | 4/1958 | Hale | 128/78 |
| 3,171,409 | 3/1965 | Cetrone | 128/112.1 X |
| 3,343,533 | 9/1967 | Hulben | 128/112.1 X |
| 3,603,316 | 5/1971 | Lehman . | |
| 3,605,731 | 9/1971 | Tigges | 128/78 X |
| 4,294,239 | 10/1981 | Oram et al. | 128/96.1 |
| 4,348,774 | 9/1982 | Woodson . | |
| 4,384,372 | 5/1983 | Rector . | |
| 4,545,370 | 10/1985 | Welsh . | |
| 4,685,668 | 8/1987 | Newlin, Jr. . | |
| 4,768,499 | 9/1988 | Kemp . | |

OTHER PUBLICATIONS

CompVest Back Support Brochure, Comp Equipment Corporation, Sep./Oct. 1985 [Sizes and Colors].

Primary Examiner—Robert A. Hafer
Assistant Examiner—Kerry Owens
Attorney, Agent, or Firm—Wood, Herron & Evans

[57] ABSTRACT

A rigid abdominal pad is disclosed as an accessory for a conventional weight lifters belt or the like and which when held against the abdomen to provide a bearing surface therefor reduces the risk of back or spinal injury arising from lifting heavy objects.

53 Claims, 3 Drawing Sheets

RIGID ABDOMINAL PAD FOR LUMBAR/SACRAL SUPPORT

This application is a continuation, of application Ser. No. 07/275,789 filed Nov. 23, 1988, abandoned.

BACKGROUND OF THE INVENTION

I. Field of the Invention

The present invention relates to a rigid abdominal pad for a lumbar/sacral support to decrease the risk of back or spinal injury arising from lifting heavy objects, for example.

II. Description of the Prior Art

Musculoskeletal disorders are some of the more common impairments in both male and female populations. Disorders of the back and spine make up the largest fraction of the total category of musculo-skeletal problems. These conditions also rank first in cost outlays by industry. As a result, musculoskeletal disorders are among the most important disease categories affecting both industrial economies and various U.S. health reimbursement systems.

Indeed, low back pain is often believed to be one of the most common causes of absence from work in today's work force. It has also been estimated that about 20% of all occupational injuries in the U.S. are back related and that about 70–80% of the world's population will have suffered this type of orthopedic problem sometime during their life.

Additional difficulties arise when the related cost of back problems occur. Taking into account the average hospital cost, salary compensation, disability payments and replacement expenses, the back ache poses itself as a destructive pathology in the American workplace. It has been estimated that such costs may be as high as $30 billion annually.

The etiology of back injuries are directly related to muscular-skeletal disuse and misuse syndromes, as well as the incidence of unpreventable trauma. Chronic stress and strain demonstrated over a period of years account for many degenerative related back pathologies. The results of general muscular-skeletal disuse and misuse manifest the eventual disruption of the vertebral bodies resulting in micro-fractures, herniation, and disk degeneration.

Certain of the risks of lower back pain and/or injury may be minimized by selecting appropriate individuals to perform the task. It is also desirable to provide education and training in the proper methods of lifting. However, these approaches are not widespread or properly followed in many instances and thus do not add much to the prevention of industrial back injuries.

A more promising approach to reducing the risk of lower back injuries has come from the recognition that the human trunk or torso functions similarly to a resilient cylinder which can be made to stiffen or relax. As the cylinder stiffens, the stress on any given portion of the cylinder tends to spread out over the whole of the cylinder thereby reducing the stress at the given location. This situation similarly occurs in the human body, whereby as the intra-abdominal pressure (IAP) of the torso increases, the load on the human trunk is transferred from the back to the abdominal cavity. Specifically, (1) the spine is essentially a segmented column supported by the paraspinal musculature which attaches anteriorly to both the thoracic and abdominal cavities; (2) actions of the muscles through movement creates a rigid mass with the capability of transferring forces from the spine to the trunk; (3) contraction of the trunk musculature creates a system of pressurized rigid chambers in the thorax and abdominal cavities which are filled with air and a semi-fluid mass, respectively; and (4) IAP increases with the strain of muscle contraction.

It has been known to artificially induce some increase in IAP by compressing the abdomen with a belt or corset tightened about the waist. An example is the well-known weight-lifters belt which is generally comprised of a leather strap with a widened portion adapted to be situated over the wearer's back and across the spine. Another device promoted widely for industry is known as the CompVest back support available from Comp Equipment Corporation, 1473 Energy Park Drive, St. Paul, MN 55108. The CompVest device is made of a light weight nylon mesh with anterior velcro closures and has a front portion adapted to be situated between the ribs and the pelvic bone and a rear portion adapted to overlie the back and spine and the upper buttocks.

With the conventional weight lifters belt or the CompVest device, tightening of the device about the waist has been suggested to increase IAP thus shifting some of the load from the spine to the abdominal cavity. However, even with the increase in IAP induced by compressing the waist, the stresses associated with lifting even normally encountered loads is believed to require more support than is provided by the belt or vest device. Specifically, it is believed that the spine and the trunk musculature must still bear an inordinate load thereby not sufficiently reducing risk of lower back pain and/or injury during normal lifting procedures. Similarly, the musculature is thus strained any may fatigue or become injured.

Some belts or corsets have also been utilized to force proper posture for lifting. For example, a conventional weight lifters belt does not Pat. No. 4,543,370 proposes to modify such a belt by equipping it with a wide front portion which contacts or overlies the sternal half of the tenth rib and the anterior portion of the iliac cost in the pelvis. The wide front portion acts to restrict excessive forward bending and thus promotes proper lifting posture. While forcing the abdomen to remain substantially straight, the approach suggested by Welsh to accomplish this result is not believed to be desirable. Contact by the front of the belt with the bony prominences about the abdomen in generally uncomfortable and may cause injury or lead users to stop wearing the belt. Further, that contact may lead to loss of consistent pressure distribution within the abdominal cavity. Such contact also limits the extent to which the front of the belt may be tightened against the abdomen. Hence, to promote proper posture as suggested in the Welsh patent may reduce the benefit available with a conventional weight lifters belt. For example, to obtain desired increases in IAP may require that the musculature absorb even more of the load then may be required of conventional weight lifters belts. Thus, in view of the state of the art, there is definitely a present need for a device which can increase intra-abdominal pressure and promote proper posture while reducing risk of injury or fatigue.

SUMMARY OF THE INVENTION

We believe that greater intra-abdominal pressure increases may be induced with less risk of injury than provided by the above devices. We further believe that proper lifting posture may be promoted without the drawbacks encountered by contact with abdominal bony prominences. In its broadest sense, the present invention accomplishes these desirable ends by the provision of an accessory for a conventional weight lifters belt or the like by which to provide a rigid bearing surface for a substantial portion of the abdomen during lifting. Specifically, we provide a rigid pad sized to fit between a person's. Abdominal bony landmarks and having a generally flat surface to mate with and overlie a substantial portion of the abdomen such that the belt or similar structure sandwiches the pad between the belt and the fleshy portion of the abdomen. Preferably, the pad is mounted to a conventional weight lifters belt.

In contrast to a weight lifter's belt and the CompVest device, the pad of the present invention is inflexible and, thus, will not tend to warp or twist or otherwise deform when the abdomen bears against it during lifting Hence, the rigid pad provides for uniform compression over the abdomen when the belt is tightened. Further, the pad provides a stiff surface against which the abdomen bears during lifting thereby urging the torso to maintain a generally linear orientation which cannot readily bend or flex about the longitudinal axis of the rigid pad such as is otherwise possible with a conventional weight lifters belt for example. Thus, rather than rely upon contraction of the trunk musculature to increase IAP as the person attempts to lift a load, the abdomen may bear firmly against the surface of the rigid pad to increase IAP, thereby relieving the spine and musculature of part of the load. In particular, the pad of the present invention is believed to provide a substitute "wall" to induce an increase in IAP with less musculature tension or effort in the torso than previously required. The increased IAP with less trunk musculature contraction is believed to advantageously reduce stress or strain on the lumbar/sacral area thereby reducing risk of lower back pain or injury while also limiting the risk of fatigue or injury to the musculature.

In a preferred embodiment, the pad provides a substantially flat surface which extends over a substantial fleshy portion of the abdomen and between the bony prominences about the abdomen such that as the wearer of the pad bends to lift a load, the bony prominences move into or toward the edge of the pad. To avoid discomfort, the surface of the pad flares away from the body at the edges or corners adjacent the bony prominences. Thus, the surface of the pad preferably extends over most of the abdomen between the ribs and pubis with the angled corners extending from the lateral edges of the pad so as to lie outwardly of and angled away from the abdominal bony prominences. In this way, the abdomen may bear against the pad without the pad also undesirably contacting abdominal bony prominences. In a preferred embodiment where the pad is rectangular in shape, notches or gaps are cut into the pad between pairs of the angled corners extending from the corners to define strap slots along the sides of the pad through which the strap of the belt may be snugly received to thereby mount the pad to the belt.

Experimental studies with a rigid pad according to the principles of the present invention show it to be effective in enhancing force production of the torso of the humans tested and, thus, suggests that lower back pain and/or injury can be reduced to a level and extent not previously thought possible or achieved.

These and other objects and advantages of the invention shall be made apparent from the accompanying drawings and the description thereof.

BRIEF DESCRIPTION OF THE DRAWINGS

The accompanying drawings, which are incorporated in and constitute a part of this specification, illustrate a preferred embodiment of the invention and, together with a general description of the invention given above, and the detailed description of a preferred embodiment given below, serve to explain the principles of the present invention.

DETAILED DESCRIPTION OF THE DRAWINGS

Figure 1:
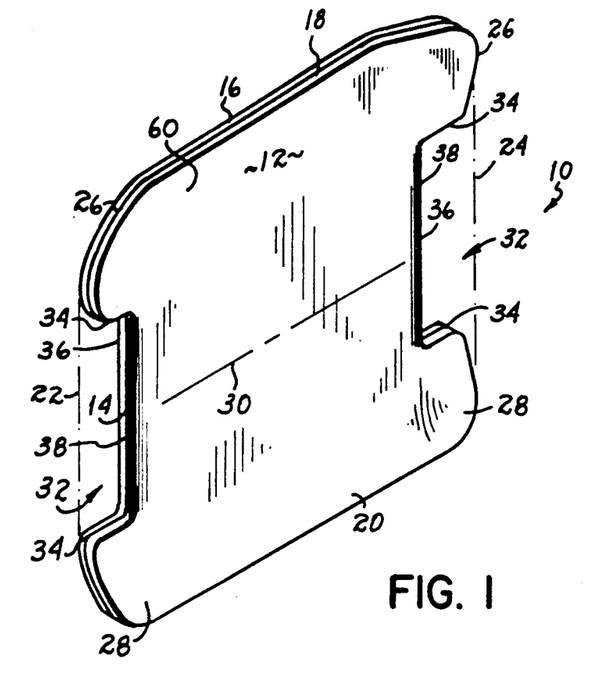
FIG. 1 is a perspective view from the front of a preferred embodiment of an abdominal pad constructed in accordance with the principles of the present invention.
Figure 2:
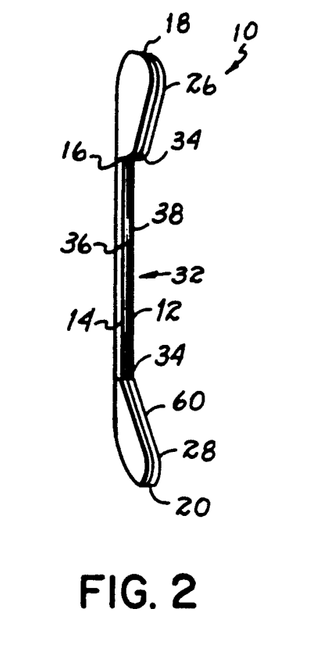
FIG. 2 is a side elevational view of the abdominal pad of FIG. 1.
Figure 3:
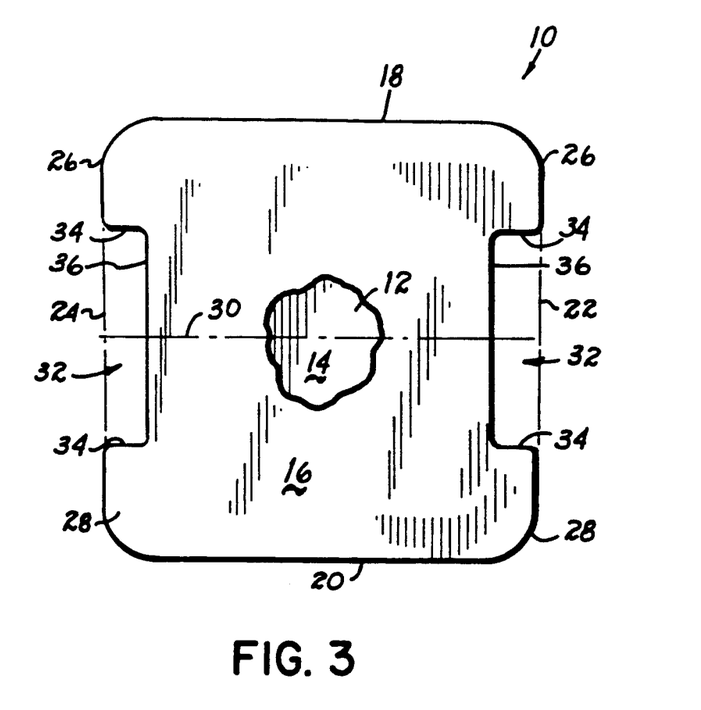
FIG. 3 is a partially cutout, rear elevational view of the pad of FIG. 1.

With reference to FIGS. 1-3, there is shown a rigid abdominal pad 10 constructed in accordance with tee principles of the present invention. Pad 10 includes a rigid plate 12 having an outer bearing surface 14. Conforming to plate 12 upon bearing surface 14 may be an outer cushion 16. Plate 12 may be formed from a ¼ inch thick stiff plastic such as polypropylene. Cushion 16, which overlies bearing surface 14 and conforms to the shape of plate 12, provides a comfort surface for the user and may be formed from a 3/16 inch thick slab of aliplast secured to plate 12 such as by glue (not shown).

Bearing surface 14 is defined between longitudinal superior or upper edge 18 and inferior or lower edge 20 and lateral left and right edges 22, 24, respectively. The dimension of pad 10 between those edges is selected for proper anatomical fit and comfort against the human abdomen (see FIGS. 5 and 6) so as to overlie a substantial portion of the abdomen between the pubic symphysis and xiphoid or lowest part of the ribs on the one hand and the iliac prominences or crests on the other hand, i.e., between the bony prominences about the abdomen. Between these bony landmarks of the abdomen is an area of the abdomen that does not closely overlie any bone structure. This area is referred to herein as the fleshy portion of the abdomen. Preferably pad 10 is sized to overlie a substantial portion of this fleshy portion. The following is a table of preferred dimensions, in inches, of pad 10 for various size men and women wherein vertical is between edges 18 and 20 and width is between edges 22 and 24:

|  | SMALL | MEDIUM | LARGE | X-LARGE |
| --- | --- | --- | --- | --- |
|  |  | MEN |  |  |
| Vertical | 4½ | 6¼ | 7 | 7½ |
| Width | 5 | 6¼ | 7¼ | 7½ |

|          | SMALL | MEDIUM | LARGE | X-LARGE |
|----------|-------|--------|-------|---------|
|          |       | WOMEN  |       |         |
| Vertical | 4¼    | 6      | 6¼    | 6¾      |
| Width    | 5½    | 7      | 7¼    | 7¾      |

Thus, pad 10 generally is between our to seven inches measured vertically and five to eight inches measured horizontally.

To avoid impinging the bony prominences or snagging any skin or fat about the abdomen while using pad 10, pad 10 is provided with transition zones at the periphery thereof. These transition zones are preferably accomplished by angling the upper and lower corners 26, 28 of pad 10 away from bearing surface 14. Due to the size of pad 10, corners 26, 28 would, if planar to surface 14, undesirably impinge against abdominal bony prominences during lifting. However, corners 26, 28 are sufficiently angled so as to extend over and away from such bony prominences so that as the user bends, undesirable contact with bony prominences 84 is avoided. In particular, superior corners 26 flare away from the subcostal angles of the human ribs 94 so as not to impinge on the ribs during lifting. Similarly, inferior corners 28 flare away from the pubis to avoid impinging the pelvic 96 or hip bones during lifting. Further, the entire inferior edge 20 preferably flares away from surface 14 to avoid impinging against the pelvis and, in particular, the iliac prominences or crests during lifting. Upper edge 18 may also have a slight flare to avoid impinging against the upper abdomen during lifting.

In a preferred embodiment, C-shaped notches 32 are formed in pad 10 between each pair of corners 26, 28 to receive a strap portion of a belt as will be discussed. C-shaped notches 32 are defined between generally parallel, upper and lower edges 34 at corners 26, 28 and perpendicular bight edges 36 therebetween. Bight edges 36 are preferably bevelled away from bearing surface 14 as at 38 to allow the belt strap portion to better conform to pad 10.

Figure 4:
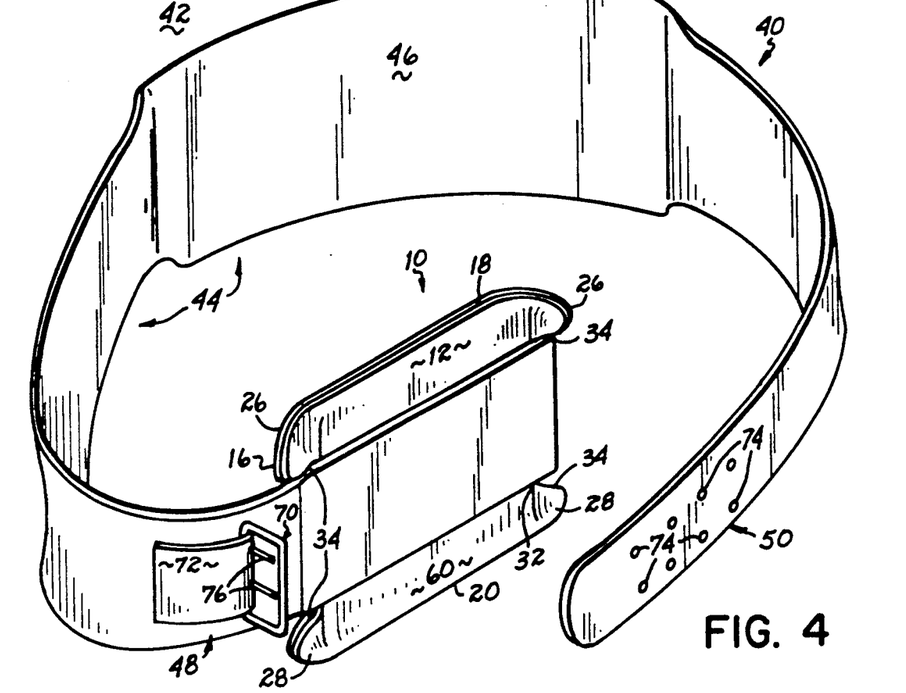
FIG. 4 is a perspective view of the abdominal pad of FIG. 1 in combination with a weight lifters belt to provide a lumbar/sacral support in accordance with the principles of the present invention.

Pad 10 is preferably mounted to a retaining structure such as a conventional weight lifters belt 40 as shown in FIG. 4 to form a lumbar/sacral support 42. Belt 40 includes an elongated leather strap 44 having an enlarged or widened portion 46 centrally located between outer ends 48, 50 of strap 44. To mount one end 48 of strap 44 to pad 10, end 48 is fitted into notches 32 on pad 10 such as by being pressed into place therein between respective edges 34.

Although not necessary, belt 40 may be held to pad 10 with a clip or other retaining structure (not shown) secured to front wall or non-bearing surface 60 of plate 12. As will be appreciated, such retaining structure may take any one of a number of forms such as a resilient clip, strap or loop and pile velcro fastener, to name but a few.

To secure pad 10 against the abdomen, belt 40 may include any conventional means for fastening one end 48 to the other end 50. In the illustrative example, belt 40 is provided with a buckle 70 mounted to strap end 48 by a leather keeper 72 and a plurality of holes 74 formed in end 50 to receive teeth 76 of buckle 70 to form a conventional belt fastener. As is well understood, ends 48, 50 may alternatively be joined together by velcro fasteners with loop and keeper (not shown) or any other fastener which will permit belt 40 to be securely fastened about the waist as will now be described.

Figure 5:
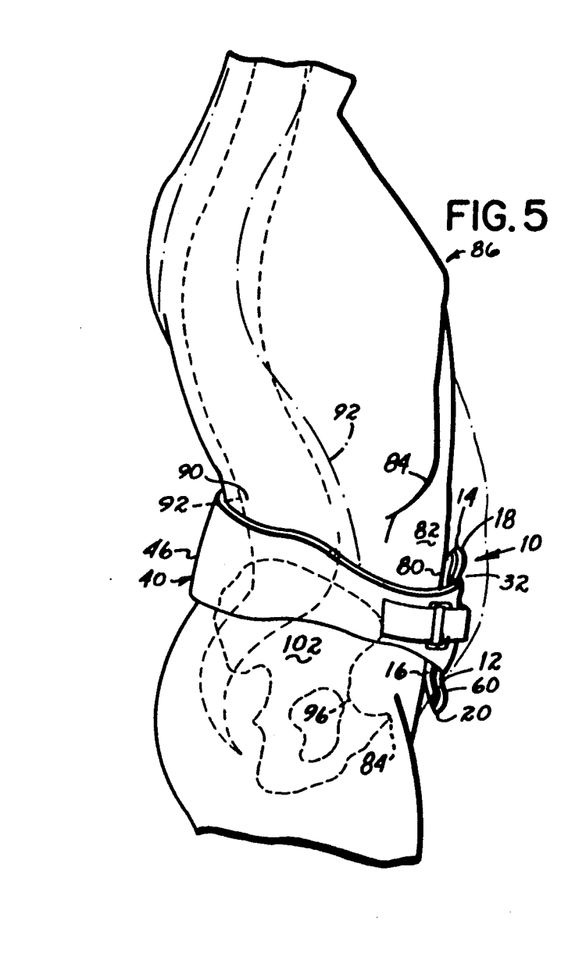
FIG. 5 is a side view of the support of FIG. properly secured about the waist of a human standing erect.
Figure 6:
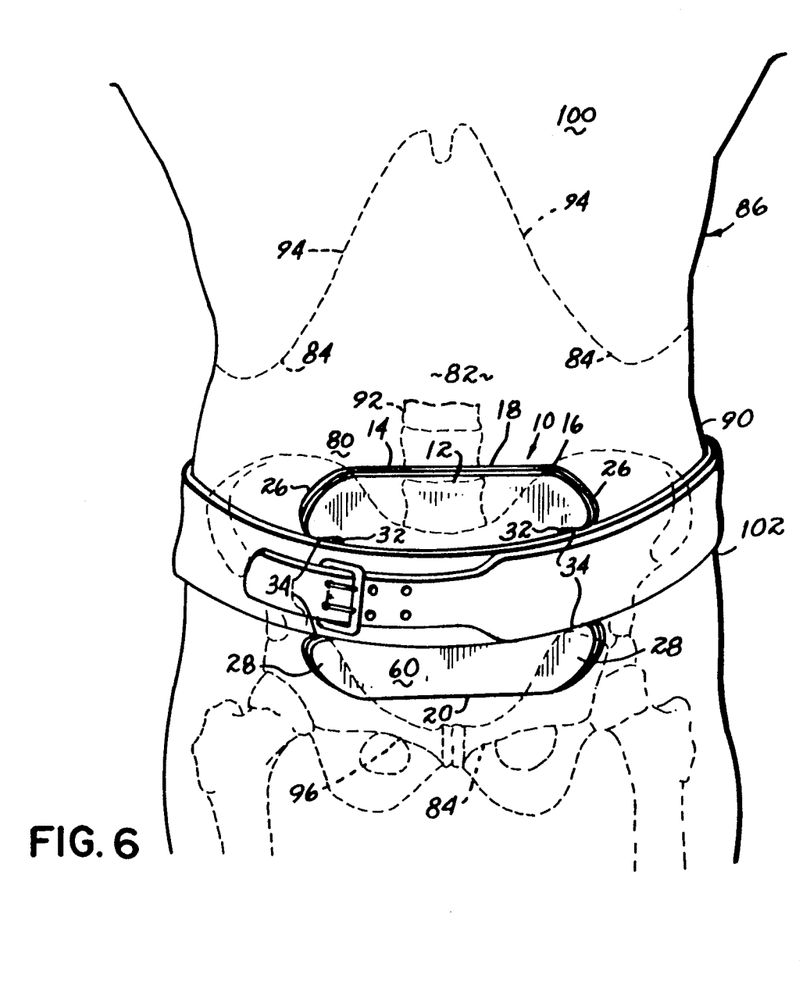
FIG. 6 is a front view of the support of FIG. 4 properly secured about the waist of a human standing erect.

Pad 10 is positioned centrally over the fleshy portion 80 of abdomen 82 and between abdominal bony prominences 84 of a human subject 86 such that bearing surface 14 of pad 10 faces the subject's abdomen 82 and corners 26, 28 are adjacent bony prominences 84. Belt 40 is placed about the human's waist 90 such that widened portion 46 of belt 40 overlies lower spine portion 92 as seen in FIG. 5 and strap ends 48, 50 overlie pad 10 to hold pad 10 over fleshy portion 80 of abdomen 82 and between the abdominal bony prominences 84 such as the xiphoid or ribs 94 and pelvis 96 as seen in FIG. 6. Although intimate contact between surface 14 and abdomen portion 80 is acceptable, cushion 16 is provided therebetween for comfort. Further, a shirt (not shown), for example, could be worn between pad 10 and abdomen 82 although cushion 16 is sufficient to provide a comfortable surface against abdomen 82. Once properly positioned, belt ends 48 and 50 are brought together and tightened in conventional manner such that abdomen portion 80 is compressed by pad 10 from its nominal outwardly-bowed orientation as shown in phantom line in FIG. 5 to a substantially planar and vertical orientation as shown in solid line in that view. Belt 40 is properly tightened when slight bending of subject 86 causes abdomen portion 80 to bear against pad 10 such that abdomen 82 is restrained from bending or flexing about longitudinal axis 30 of pad 10.

Figure 7:
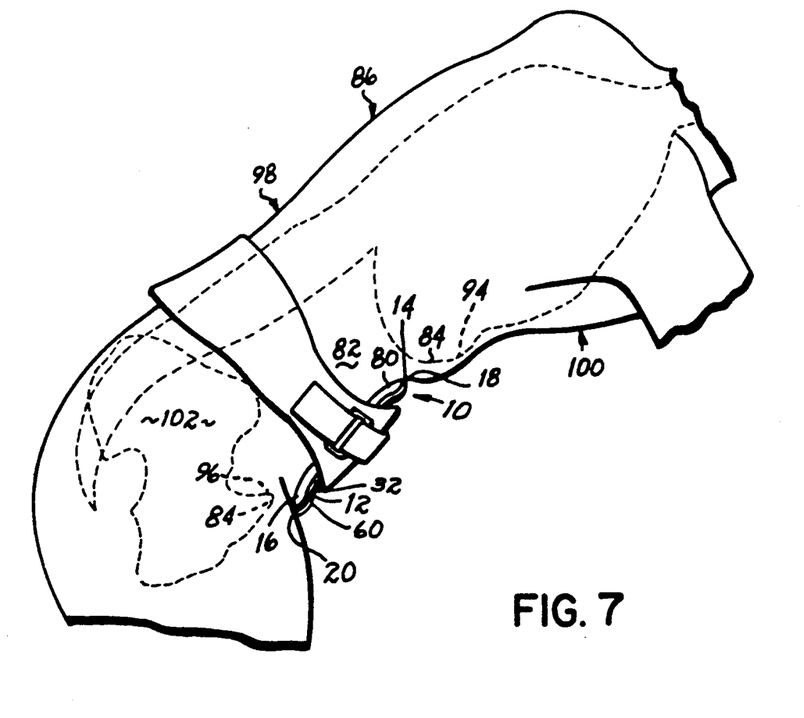
FIG. 7 is a view like FIG. 5 showing the human abdomen bearing against the pad of FIG. 1 in response to lifting stresses as contemplated by the present invention.

As subject 86 tries to bend at the waist as shown in FIG. 7, abdomen portion 80 will bear against surface 14 of pad 10. This bearing contact will tend to prevent the abdomen from bending thus encouraging proper lifting posture by urging trunk 98 into a substantially linear orientation between the chest 100 and hips 102. And as the trunk 98 rotates between positions shown in FIGS. 5 and 7, the flaring of corners 26, 28 prevent undesirable contact with bony prominences and further avoids biting contact between pad 10 and any flesh or fat about the abdomen. Similarly, flaring of inferior edge 20 reduces biting contact between pad 10 and the pubic area of the human as might otherwise occur if edge 20 were not flared.

In use, as subject 86 bends over and tries to lift a load (not shown), abdomen portion 80 will bear against surface 14 of pad 10. Pad 10 is believed to provide a wall which substitutes for trunk musculature contraction to thereby increase IAP without undue musculature activity in the abdomen. The result is an increase in lifting capacity which is believed to be attained with reduced risk of pain or injury to the spine by better spreading stress from the spine to the abdomen without injuring or fatigue of the musculature. That is, the present invention is believed to result in elevating IAP without placing an undue load or stress on the abdominal wall muscles. Thus, instead of relying upon the musculature to contain and compress the abdomen to transfer force from the spine, the rigid pad 10 is provided for this purpose.

The particular shape of pad 10 is of further advantage in providing a maximally stiff and large plate 12 to compress as much of abdomen 82 as possible while avoiding the discomfort, potential injury and limitation which may result from contact with abdominal bony prominences.

EXAMPLES

Ten well-conditioned males between the ages of 21 and 35 undergo isokinetic back testing under three conditions. Each of the subjects is tested without any support (control), with a CompVest device, and with a support comprised of a rectangular rigid pad held to the abdomen according to the principles of the invention (experimental support).

Reduction in trunk flexion forces is believed to be indicative of increased IAP. The isokinetic back tests demonstrate trunk flexion forces at various speeds of isokinetic resistance with the pad as compared to the CompVest device and no device. The results are statistically highly significant for the various measures of average muscle torque, work and power for trunk flexion at 30° per second as shown in

TABLE I

| Measure | CompVest | Experimental Support | Control |
|---|---|---|---|
| Torque/Newton Meters | 213.43 | 200.95 | 222.92 |
| Work/Newton Meters | 262.38 | 246.24 | 272.42 |
| Power/Watts | 90.30 | 84.50 | 94.00 |

Measures at higher speeds of isokinetic resistance (60°/sec., 90°/sec. and 120°/sec.) are also found to be statistically significant with the experimental support. Trunk rotation of muscle torque is also statistically significant. Also, grand means for peak lifting force (Table II) and lifting power (Table III) are found to be higher when subjects perform the lifting task with the pad than without. The increase in these measures are consistent with increased trunk forces obtained during trunk extension trials when subjects wear the pad as compared to the control:

TABLE II

GRAND MEANS AND STANDARD DEVIATIONS FOR PEAK LIFTING FORCES
(Values Expressed in Newtons)

| Speed of Resistance | Mean/SD CompVest | Mean/SD Experimental Support | Mean/SD Control |
|---|---|---|---|
| 30 inches/sec | 1373.71 (318.70) | 1420.44 (290.71) | 1325.21 (322.35) |

TABLE III

GRAND MEANS AND STANDARD DEVIATIONS FOR LIFTING POWER
(Values Expressed in Watts)

| Speed of Resistance | Mean/SD CompVest | Mean/SD Experimental Support | Mean/SD Control |
|---|---|---|---|
| 30 inches/sec | 732.60 (211.32) | 766.60 (177.16) | 712.20 (171.01) |

The results suggest that the capacity to increase lifting forces are enhanced with the present invention. The results also suggest that the present invention provides increases in IAP with less stress on the musculature than provided by the prior art. The results further suggest that less musculature activity is required to lift the same load with a pad according to the invention than with the CompVest device of the prior art or with no support. This is believed to reduce stress on the back or spine and, thus, reduce risk of injury thereto. It is also believed that if the musculature were to become more involved, the present invention would result in an even greater IAP than possible with prior art devices, thereby further reducing stress on the back Further analysis and detail of such studies may be found in the thesis prepared by Michael L. Woodhouse, one of the inventors herein, entitled "The Effects of Various Lumbar/Sacral Back Support Systems Upon Human Peak Muscular Force, Total Work, and Average Power" submitted to the faculty of Old Dominion University. The thesis is incorporated herein by reference and a copy is submitted with this application for patent.

Additional advantages and modifications will readily appear to those skilled in the art. The present invention in its broader aspects is therefore not limited to the preferred embodiment and illustrated example shown and described. Accordingly, departures may be made from such details and/or departing from the spirit or scope of the present invention.

Having described the present invention, what is claimed is:

1. An abdominal pad for supporting the sacrolumbar regions of a human when the human is lifting an object, the abdominal pad comprising:

a rigid place having a planar and substantially non-yielding surface sized to valerie a substantial fleshy potion of the human's abdomen between the human's abdominal bony prominences; and a layer of generally flat cushion material fixed to said rigid plate in conforming relationship to provide a comfort layer between the human's abdomen and said rigid plate, said rigid plate and aid layer cooperating to define the abdominal pad, the abdominal pad providing a bearing surface for the substantial fleshy portion to generally uniformly and effectively bear thereagainst without impinging the human's abdominal bony prominences, the abdominal pad providing an increase in intra-abdominal pressure when t he human is lifting an object such that the human's sacrolumbar regions are effectively supported.

2. The abdominal pad of claim 1, said rigid plate being comprised of stiff plastic.

3. The abdominal pad of claim 1, said rigid plate having a vertical dimension and a horizontal dimension, said vertical dimension being between approximately five to eight inches and said horizontal dimension being between approximately four to seven inches.

4. The abdominal pad of claim 1, said layer being a slab of aliplast.

5. The abdominal pad of claim 1, said rigid plate having a periphery, the abdominal pad further comprising:

angled corners about said periphery at locations adjacent the abdominal prominences and flaring away from the human to avoid impinging the human's abdominal bony prominences about the substantial fleshy portion of the human's abdomen when the human is lifting an object.

6. The abdominal pad of claim 5, said rigid plate being substantially rectangular, said angled corners being at respective corners of said rectangular rigid plate.

7. The abdominal clad of claim 5 further comprising:

a C-shaped slot defined between confronting edges of at least one pair of said angled corners and an edge of said rigid plate extending between aid one pair of angles corners, said slot being sized to snugly receive therein a strap of a belt-like support structure.

8. The abdominal pad of claim 1 further comprising:

mounting means for mounting said rigid plate to a belt-like support structure.

9. The abdominal pad of claim 8, said mounting means including:
 a slot defined adjacent an edge of said rigid plate for receiving therein a portion of the belt-like support structure.

10. The abdominal pad of claim 9, said slot having a bight edge bevelled away from said layer.

11. The abdominal pad of claim 8, said rigid plate having a periphery, said mounting means including:
 at least one pair of corners about said periphery at locations adjacent the human's abdominal bony prominences and flaring away from he human to avoid impinging the human's abdominal bony prominences about the substantial fleshy portion of the human's abdomen when the human is lifting an object; and
 a C-shaped slot having an upper and a lower edge and a bight edge therebetween, the upper and lower edges defined by confronting edges of said one pair of centers, said bight edge being an edge of said rigid plate extending between said one pair of angles corners, said slot for receiving therein a portion of the belt-like support structure.

12. The abdominal pad of claim 11, said slot bight edge being bevelled away from said layer.

13. The abdominal pad of claim 1, said rigid plate having a bottom edge and a depending surface theralong, he depending surface being flared away from the human to avoid biting contact with the human when t he human is lifting an object.

14. A lumbar sacral support comprising:
 the abdominal pad of claim 1; and
 retaining means for retaining said rigid plate against the human's abdomen such that the human's abdomen bears against said planar and substantially non-yielding surface when the human is lifting an object.

15. The lumbar/sacral support of claim 14 wherein said retaining means including a belt-like structure.

16. The lumbar/sacral support of claim 15, said belt-like structure is a weight lifers belt.

17. The lumbar/sacral support of claim 15, said retaining means further including a sot defined along an edge of said rigid plate for receiving therein a portion of said belt-like structure.

18. The lumbar/sacral support of claim 17, said slot having a bight edge bevelled away from said layer.

19. The abdominal pad of claim 1, said rigid plate further having a bottom edge and a depending surface therealong, said depending surface being flared away from the human to a void biting contact with the human when the human is lifting an object.

20. An abdominal pad for supporting the sacrolumbar regions of a human when the human is lifting an object, the abdominal pad comprising:
 a rigid plate having a planar and substantially non-yielding bearing surface sized to overlie the substantial fleshy portion of the human's abdomen between the human's abdominal bony prominences for providing an effective bearing surface for the substantial fleshy portion to bear thereagainst, said rigid plate providing an increase in intra-abdominal pressure when the human is lifting an object such that the human's sacrolumbar regions are supported, said rigid plate further having a bottom edge and a depending surface theralong, the depending surface being flared away from the human to avoid bight contact with the human during lifting.

21. The abdominal pad of claim 20, said rigid plate having a vertical dimension and a horizontal dimension, said vertical dimension being between approximately five to eight inches and said horizontal dimension being between approximately four to seven inches.

22. The abdominal pad of claim 20, said rigid plate having a periphery, the abdominal pad further comprising:
 angled corners about said rigid plate periphery at locations adjacent the human's abdominal bony prominences and flaring away from the human to avoid impinging the human's abdominal bony prominences about the substantial fleshy portion of the human's abdomen when the human is lifting an object.

23. The abdominal pad of claim 22, said rigid plate further including:
 a C-shaped slot having an upper and a lower edge and a bight edge therebetween, the upper and lower edges defined by a pair of confronting edges of at least one pair of said corners, said bight edge being an edge of said rigid plate extending between said one pair of angled corners, said lost for receiving therein a portion of said belt-like structure.

24. The abdominal pad of claim 23, said slot bight edge being bevelled away for said bearing surface.

25. The abdominal pad of claim 20 further comprising:
 mounting means for mounting said rigid plate to a belt-like support structure.

26. The abdominal pad of claim 25, said mounting means including:
 a Cshaped slot having a bight edge defined by a vertical edge of said rigid plate.

27. The abdominal pad of claim 26, said bight edge being bevelled away from said bearing surface.

28. A lumbar/sacral support comprising:
 the abdominal pad of claim 20; and
 retaining means for retaining said rigid plate against the human's abdomen such that the human's abdomen bears against said bearing surface when the human is lifting an object.

29. An abdominal pad for supporting the sacrolumbar regions of a human when the human is lifting an object, the abdominal pad comprising:
 a rigid plate having a planar and substantially non-yielding bearing surface sized to overlie a substantial fleshy portion of the human's abdomen between the human's abdominal bony prominences for providing an effective bearing surface for the substantial fleshy portion of the human's abdomen to bear thereagainst, said rigid plate providing an increase in intra-abdominal pressure when the human lifts an object such that the human's sacrolumbar regions are effectively supported, said rigid plate further having a periphery and corner surfaces about said rigid plate periphery at locations adjacent the human's abdominal bony prominences, the corner surfaces being flared away from the human to avoid impinging the human's bony abdominal prominences when the human is lifting an object.

30. The abdominal pad of claim 29 further comprising:
 slot means extending along a portion of said rigid plate periphery and between a pair of the corner surfaces for receiving therein a strap of a belt-like support structure.

31. The abdominal pad of claim 29, said rigid plate having a vertical dimension and a horizontal dimension, said vertical dimension and a horizontal dimension, said vertical dimension being between approximately five to eight inches and said horizontal dimension being between approximately four to seven inches.

32. The abdominal pad of claim 29 further comprising:
mounting means for mounting said rigid plate to a belt-like support structure.

33. The abdominal pad of claim 32, said rigid plate further including:
a C-shaped slot having an upper and a lower edge and a bight edge therebetween the upper and lower edges defined by a pair of confronting edges of at least one pair of said corners, said bight edge being an edge of said rigid plate extending between said one pair of angled corners, said slot for receiving therein a portion of said belt-like structure.

34. A lumbar/sacral support comprising: the abdominal pad of claim 29; and
retaining means for retaining said rigid place against the human's abdomen such that the human's abdomen bears gain st said bearing surface.

35. A method for supporting the sacrolumbar regions of a human when the human is lifting an object, said method comprising:
compressing a planar and substantially non-yielding bearing surface of a rigid plate against a substantial fleshy portion of the human's abdomen between the human's abdominal bony prominences to generally and uniformly effectively compress the substantial fleshy portion of the human's abdomen so as to provide an increase in the intra-abdominal pressure as the human lifts an object such that the human's a sacrolumbar regions are supported.

36. The method of claim 35 further comprising:
sandwiching the rigid plate between the human's abdomen an a belt encircling the human's waist whereby to hold the rigid plate's surface against the human's abdomen when the human is lifting an object.

37. The method of claim 36 further comprising:
providing slots in opposite edges of the rigid plate and receiving portions of the belt in the slots.

38. The method of claim 37 further comprising:
providing said slots in Cshape along opposed vertical edges of the rigid plate such that each vertical edge defines a bight edge of a respective slot.

39. The method of claim 35 further comprising:
flaring corners of the rigid plate away from the human and over the human's abdominal bony prominences to avoid undesirable contact therewith by the rigid plate when the human is lifting an object.

40. The method of claim 39 further comprising:
flaring an inferior edge of the rigid plate away from eh human to avoid biting contact with the human when the human is lifting an object.

41. The method of claim 35 further comprising:
flaring an inferior edge of the rigid plate away from the human to avoid biting contact with the human when the human is lifting an object.

42. The method of claim 35 further comprising:
fixing a layer of generally flat cushion material in conforming relationship to the rigid plate.

43. An abdominal pad for supporting the sacrolumbar regions of a human when the human is lifting an object, said pad comprising:
a rigid late having a generally flat and substantially non-yielding front surface sized to overlie a substantial fleshy portion of a human abdomen between abdominal bony prominences for providing an effective bearing surface for the substantial fleshy portion of the human abdomen to bear thereagainst and for providing support for the sacrolumbar regions during lifting, the plate further having an upper and a lower corner flaring away from the human, each corner extending beyond a vertical edge of the plate to define a C-shaped slot having a bight edge defined by the vertical edge, the slot being between the corners sized to receive therein a strap of a belt-like support structure.

44. The abdominal pad of claim 43, said plate having a vertical dimension and a horizontal dimension, said vertical dimension being between approximately five to eight inches and said horizontal dimension being between approximately four to seven inches.

45. The abdominal pad of claim 43, said bight edge being bevelled away from the bearing surface.

46. The abdominal pad of claim 43, said rigid plate further having a bottom edge and a depending surface theralong, said depending surface being flared away from the human to avoid biting contact with the human when the human is lifting an object.

47. An abdominal pad for supporting the sacrolumbar regions of a human when the human is lifting an object, the abdominal pad comprising:
a rigid late having a planar and substantially non-yielding bearing surface sized to valerie the substantial fleshy portion of the human's abdomen between the human's abdominal bony prominences for providing an effective bearing surface of the substantial fleshy portion to bear thereagainst, said rigid plate further providing an increase in intra-abdominal pressure when the human is lifting an object such that the human's sacrolumbar regions are effectively supported.

48. An abdominal pad for supporting the sacrolumbar regions of a human when the human is lifting an object, said pad comprising:
a first layer of generally flat rigid material sized to overlie a substantial fleshy portion of the human's abdomen between the human's abdominal bony prominences; a second layer of generally flat cushion material fixed of the first layer in conforming relationship to provide a confront layer between the human's abdomen and the first layer, the first and second layers cooperating to define a generally rigid plate having a generally flat and substantially non-yielding surface for the substantial fleshy portion of the human's abdomen to generally uniformly and effectively bear thereagainst without impinging the human's abdominal bony prominences and to provide support to the human's sacrolumbar regions when the human is lifting an object;
said fist layer having a periphery and angles corners about said periphery at locations adjacent the human's abdominal bony prominences and flaring away from the human to avoid impinging the human's abdominal bony prominences about the substantial fleshy portion of the human's abdomen during lifting; and a C-shaped slot defined between confronting edges of at least one pair of said angled corners and an edge of said first layer extending between said one pair of angled corners, said lost being sized to snugly receive therein a strap of a belt-like support structure.

49. An abdominal pad for supporting the sacrolumbar regions of a human when the human is lifting an object, said abdominal pad comprising:

a first layer of generally flat rigid material sized to overlie a substantial fleshy portion of the human's abdomen between the human's abdominal bony prominences;

a second layer of generally flat cushion material fixed of the first layer in confirming relationship topside a comfort layer between the human's abdomen and the first layer, the first and second layers cooperating to define a generally rigid plate having a generally flat and substantially non-yielding surface of the substantial fleshy portion of the human's abdomen to generally uniformly and effectively bear therragainst without impinging the human's abdominal bony prominences and to provide support to the human's sacrolumbar regions when the human is lifting an object;

mounting means for mounting said plate to a belt-like support structure; and said first layer having a periphery and at least one pair of corners about said periphery at locations adjacent the human's abdominal bony prominences and flaring away from the human to avoid impinging the human's abdominal bony prominences about the substantial fleshy portion of the human's abdomen during fiting and a C-shaped slot having an upper and a lower edge and a bight edge therebetween, the upper and lower edges defined by confronting edges of said one pair of corners, said bight edge being can edge of said first layer extending between said one pair of angled corners, said slot for receiving therein a portion of the belt-like support structure.

50. The abdominal pad of claim 49, said slot bight edge being beveled away from said second layer.

51. An abdominal pad for supporting the sacrolumbar regions of the human when the human is lifting an object, said pad comprising:

a rigid plate having a generally flat and substantially non-yielding front surface sized to overlie a substantial fleshy portion of human's abdomen between abdominal bony prominences for providing an effective bearing surface for the substantial fleshy portion of the human's abdomen to bear thereagainst and for providing support for the sacrolumbar regions during lifting, said rigid -late further having a bottom edge and a depending surface therealong, the depending surface being flared away from the human to avoid biting contact with the human during lifting;

said rigid plate having a periphery and angled corners about a said plate periphery at locations adjacent the human's abdominal bony prominences and flaring away from the human to avoid impinging the human's abdominal bony prominences about the substantial fleshy portion of the human's abdomen during lifting; and a C-shaped slot having an upper and a lower edge and a bight edge therebetween, the upper and lower edges defined by a pair of confronting edges of at least one pair of said corners, said bight edge being an edge of said plate extending between said one pair of angled corners, said slot for receiving therein a portion of said belt-like structure.

52. The abdominal pad of claim 51, said slot bight edge being beveled away from said bearing surface.

53. An abdominal pad for supporting the sacrolumbar regions of a human when the human is lifting an object, said abdominal pad comprising:

a rigid plate having a generally flat and substantially non-yielding front surface sized to overlie a substantial fleshy portion of the human's abdomen between the human's abdominal bony prominences for providing an effective bearing surface e for the substantial fleshy portion of the human's abdomen to bear thereagainst and for providing support for the human's sacrolumbar regions when the human lifts an object, the plate further having a periphery in corner surfaces about said plate periphery at locations adjacent the human's abdominal bony prominences, the corner surfaces being flared away from the human to avoid impinging the human's bony abdominal prominences during lifting;

mounting means for mounting said plate to a belt-like support structure; and a C-shaped slot having an upper and a lower edge and a bight edge therebetween, the upper and lower edges defined by a pair of confronting edges of at least one pair of said corners, said bight edge being an edge of said plate extending between said said one pair of angles corners, said slot for receiving therein a portion of said belt-like structure.

* * * * *

UNITED STATES PATENT AND TRADEMARK OFFICE
CERTIFICATE OF CORRECTION

PATENT NO. : 5,105,806
DATED : April 21, 1992
INVENTOR(S) : Michael L. Woodhouse, Lawrence M. Shall, Stephen M. Shall and Jack Booden, Jr.

It is certified that error appears in the above-identified patent and that said Letters Patent is hereby corrected as shown below:

Column 2, line 38, change "not Pat. No. 4,543,370" to --not generally promote proper lifting posture. Welsh U.S. Pat. No. 4,543,370--.

Column 2, line 41, change "iliac cost" to --illiac crest--.

Column 3, line 8, change "a person's. Abdominal" to --a person's abdominal--.

Column 4, line 21, change "support of FIG. properly" to --support of Fig. 4 properly--.

Column 4, line 34, change "with tee" to --with the--.

Column 8, line 20, change "a rigid place" to --a rigid plate--.

Column 8, line 21-22, change "sized to valerie a substantial fleshy potion" to --sized to overlie a substantial fleshy portion--.

Column 8, line 28, change "aid layer" to --said layer--.

Column 8, line 34, change "t he human" to --the human--.

Column 8, line 60, change "The abdominal clad" to --The abdominal pad--.

Column 8, lines 62-63, change "aid one pair of angles corners" to --said one pair of angled corners--.

Column 9, line 12, change "he human" to --the human--.

UNITED STATES PATENT AND TRADEMARK OFFICE
CERTIFICATE OF CORRECTION

PATENT NO. : 5,105,806
DATED : April 21, 1992
INVENTOR(S) : Michael L. Woodhouse, Lawrence M. Shall, Stephen M. Shall and Jack Booden, Jr.

It is certified that error appears in the above-identified patent and that said Letters Patent is hereby corrected as shown below:

Column 9, line 19-20, change "pair of centers" to --pair of corners--.

Column 9, lines 21-22, change "angles" to --angled--.

Column 9, line 28, change "he depending surface" to --the depending surface--.

Column 9, lines 29-30, change " t he human" to --the human--.

Column 9, line 31, change "lumbar sacral" to --lumbar/sacral--.

Column 9, line 39, change "including" to --includes--.

Column 9, line 41, change "weight lifers belt" to --weight lifters belt--.

Column 9, line 43, change "a sot defined" to --a slot defined--.

Column 9, line 51, change "a void" to --avoid--.

Column 10, line 1, change "bight" to --biting--.

Column 10, line 25, change "lost" to --slot--.

Column 10, line 28, change "for" to --from--.

Column 10, line 35, change "Cshaped" to --C-shaped--.

Column 11, line 5, delete "said vertical dimension and a horizontal dimension,".

UNITED STATES PATENT AND TRADEMARK OFFICE
CERTIFICATE OF CORRECTION

PATENT NO. : 5,105,806
DATED : April 21, 1992
INVENTOR(S) : Michael L. Woodhouse, Lawrence M. Shall, Stephen M. Shall and Jack Booden, Jr.

It is certified that error appears in the above-identified patent and that said Letters Patent is hereby corrected as shown below:

Column 11, line 16, insert --,-- after "therebetween".

Column 11, line 26, change "gain st" to --against"

Column 11, line 41, change "an a belt" to --and a belt--.

Column 11, line 49, change "Cshape" to --C-shape--.

Column 11, line 60, change "eh" to --the--.

Column 12, line 4, change "rigid late" to --rigid plate-.

Column 12, line 33, change "rigid late" to --rigid plate--.

Column 12, line 34, change "to valerie" to --to overlie-.

Column 12, line 37, change "surface of" to --surface for--.

Column 12, line 50, change "fixed of" to --fixed to--.

Column 12, line 51, change "a confront layer" to --a comfort layer--.

Column 12, line 61, change "angles" to --angled--.

Column 13, line 4, change "said lost" to --said slot--.

Column 13, line 15, change "confirming relationship topside" to --conforming relationship to provide--.

UNITED STATES PATENT AND TRADEMARK OFFICE
CERTIFICATE OF CORRECTION

PATENT NO. : 5,105,806
DATED : April 21, 1992
INVENTOR(S) : Michael L. Woodhouse, Lawrence M. Shall, Stephen M. Shall and Jack Booden, Jr.

It is certified that error appears in the above-identified patent and that said Letters Patent is hereby corrected as shown below:

Column 13, line 19, change "surface of" to --surface for--.

Column 13, line 22, change "therragainst" to --thereagainst--.

Column 13, line 34, change "during fiting" to --during lifting--.

Column 13, line 38, change "being can edge" to --being an edge--.

Column 14, line 3, change "rigid -late" to --rigid plate--.

Column 14, line 9, delete "a".

Column 14, line 31, delete "e".

Column 14, line 48, change "angles corners" to --angled corners--.

Signed and Sealed this

Fifth Day of April, 1994

Attest:

BRUCE LEHMAN

*Attesting Officer*    *Commissioner of Patents and Trademarks*